Figure 1:
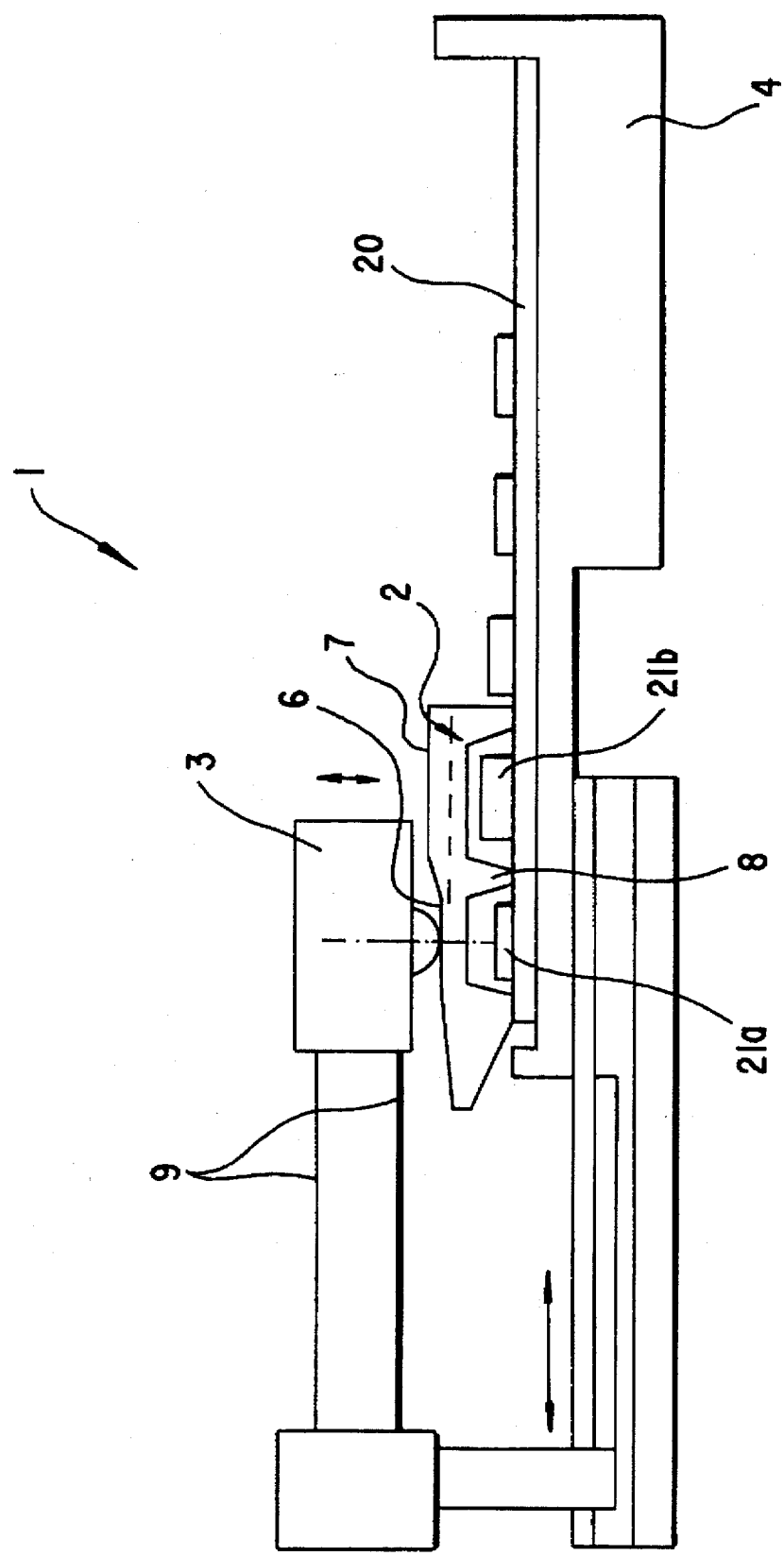

United States Patent [19]

Augstein

[11] Patent Number: 5,665,310
[45] Date of Patent: Sep. 9, 1997

[54] DEVICE WITH SPACER FOR THE REFLECTOMETRIC EVALUATION OF TEST ELEMENTS

[75] Inventor: Manfred Augstein, Mannheim, Germany

[73] Assignee: Boehringer Mannheim GmbH, Mannheim, Germany

[21] Appl. No.: 503,695

[22] Filed: Jul. 18, 1995

[30] Foreign Application Priority Data

Jul. 19, 1994 [DE] Germany .................. 44 25 432.6

[51] Int. Cl.[6] ............................................. G01N 21/01
[52] U.S. Cl. ........................ 422/66; 422/63; 422/65; 422/104; 436/43; 436/44; 436/46
[58] Field of Search .............................. 422/63, 65, 66, 422/104; 436/43, 44, 46

[56] References Cited

U.S. PATENT DOCUMENTS

| | | | |
|---|---|---|---|
| 3,645,690 | 2/1972 | Rochte et al. | 422/65 |
| 4,689,202 | 8/1987 | Khoja et al. | 422/65 |
| 4,751,184 | 6/1988 | Higo et al. | 435/287 |
| 4,826,659 | 5/1989 | Akisada | 422/63 |
| 4,876,204 | 10/1989 | Inoue et al. | 436/46 |
| 4,928,540 | 5/1990 | Kido et al. | 73/864.11 |
| 5,039,615 | 8/1991 | Takahata | 436/44 |
| 5,143,694 | 9/1992 | Schafer et al. | 422/65 |
| 5,356,595 | 10/1994 | Kanamori et al. | 422/65 |

FOREIGN PATENT DOCUMENTS

| | | |
|---|---|---|
| 0259797 A2 | 3/1988 | European Pat. Off. . |
| 0388168 A2 | 9/1990 | European Pat. Off. . |
| 0428184 A2 | 5/1991 | European Pat. Off. . |
| 2 378 277 | 8/1978 | France . |
| 59-32851 | 2/1984 | Japan . |

Primary Examiner—Long V. Le
Attorney, Agent, or Firm—Nikaido, Marmelstein, Murray & Oram LLP

[57] ABSTRACT

The invention lies in the field of analyzing sample liquids with the aid of test strips. A test strip to be analyzed is located between a test element support and a spacer. A measuring head for evaluating the test strip rests on the spacer thus ensuring a defined distance between the test field surface and the measuring head.

13 Claims, 3 Drawing Sheets

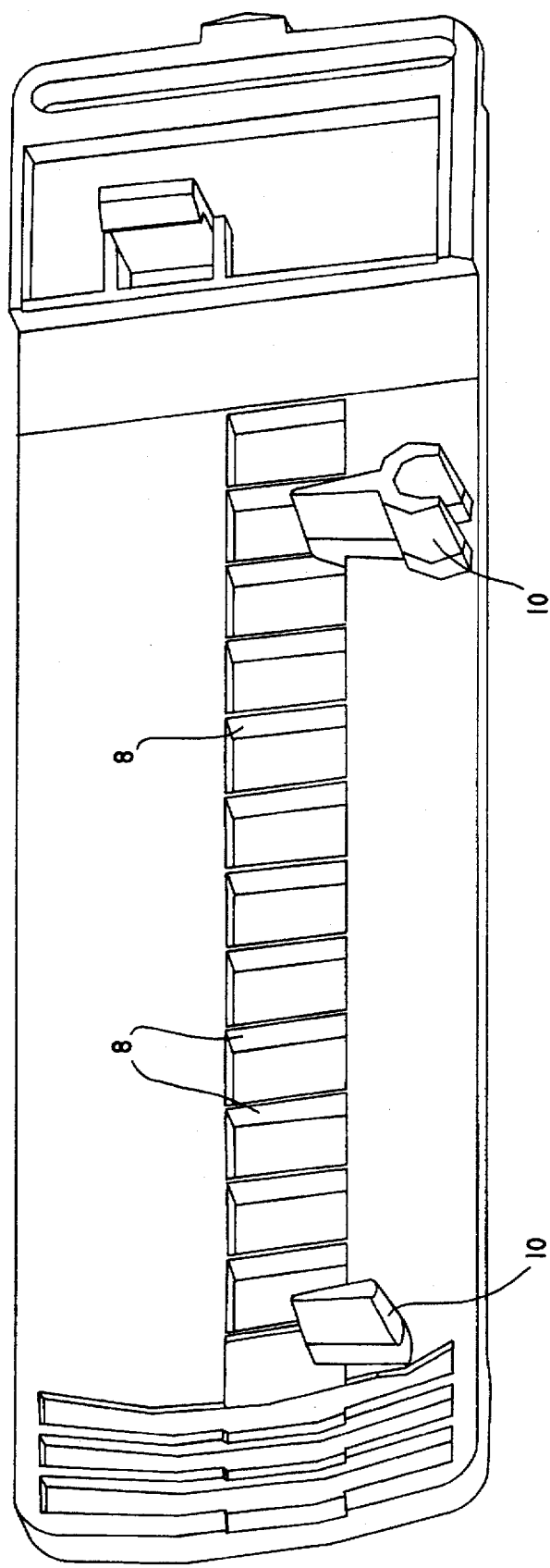

DEVICE WITH SPACER FOR THE REFLECTOMETRIC EVALUATION OF TEST ELEMENTS

The invention addresses a device for the reflectometric evaluation of test elements comprising
a measuring head with an emitter and a sensor,
a test element support onto which the test element to be analyzed is placed,
a spacer with one or several measuring openings, said spacer being located between the test element and the measuring head and defining a distance between test field surface of the test strip and the measuring head,
wherein the test element is located between the test element support and the spacer, and the measuring head rests on said spacer.

The invention lies in the field of clinical analysis where test elements, especially test strips are subject to reflectometric evaluation in order to determine the presence and concentration of certain analytes in a sample liquid.

Automated devices for the reflectometric evaluation of test strips with several test fields are known in prior art. European patent application EP-A-0 428 184 describes such an apparatus. To carry out the evaluation, the test strip to be analyzed is held by leaf springs while a measuring head having several emitting and sensing devices synchronously evaluates the test fields of the test strips. The test fields are exposed to radiation via glass fibers that are included in the measuring head. The radiation reflected by the test fields is also received by glass fibers and fed to a sensor. The fibers that transmit and receive radiation are positioned in the measuring head with the aid of screws.

A disadvantage of the prior art devices is that the evaluation of a test strip with several test fields requires numerous emitters and sensors if the distance between test field and optical measuring unit is to be considered. This means each pair of emitter and sensor must be separately adjusted in the respective position. Based on the test strip support described in EP-A-0 421 184, an exactly defined distance between measuring head and test field can only be ensured with a great deal of technical complexity as the positioning of test strip and measuring head requires a multitude of components, each of which has individual manufacturing tolerances. With such an indirect coupling of measuring head and test strip given, thermal or mechanical influences easily lead to a maladjustments.

It was an object of the invention to provide a device for evaluating test elements where the adjustment involved is reduced to a minimum, and where the setting remains stable over an extended operating time of the device. It was also an object of the invention to propose a device where the tolerances of the distance between test field and measuring head are only minor.

The invention is based upon a device for the reflectometric evaluation of test elements where the test fields are juxtaposed. The device features a measuring head comprising an emitter and a sensor, and a test element support on which the test element to be analyzed is placed and also a spacer with one or more measuring openings. During evaluation, the test element is located between the test element support, and the spacer, while the measuring head which rests on the spacer is moved from measuring opening to measuring opening.

Said device serves the purpose of evaluating test elements with test fields. Methods for evaluating sample liquids with test elements are used in particular in the area of clinical diagnostics to analyze sample liquids, such as urine, blood, serum, tissue fluid and saliva for the presence and concentration of analytes. Such test elements are also commercially available and have several test fields, e.g. 9 or 12, each of which serves to evaluate one specific analyte.

Commonly used test elements have rectangular test fields with a length of a few millimeters and a thickness of several tenth of millimeters. They are disposed adjacent to one another on a test strip support. The test strip support is usually a rectangular strip with a length of a few centimeters and a width of several millimeters. In prior art, the above-described test elements are also referred to as test strips.

These test strips may also have certain characteristics such as barcodes, alphanumerical characters and the like which are detected together with the test fields of the test strips. In accordance with the invention, it is, however, also possible that the instruments have an additional reader to identify the test strips.

With a device on which the invention is based, the test strips are exposed to radiation in the visible, the infrared or the ultraviolet range that is emitted by an emitter. To save costs, light-transmitting diodes (LEDs) are usually used as emitters. It is, however, also possible to use other emitters, if necessary together with the use of optical filters.

The radiation or a representative part thereof that is reflected by the test fields is detected by a sensor. Particularly suitable sensors are semiconductor detectors, such as photodiodes, phototransistors, or photovoltaic elements. Such sensors can be advantageously used when their sensitivity maximum matches the emission spectrum of the emitter. If necessary, the radiation entering the sensor can be selected by passing it through a filter.

In accordance with the invention, both emitter and sensor are provided in one measuring head, so that a mutual adjustment of emitter and sensor can be easily accomplished. When one single measuring head is used, it should be movable so that all measuring openings of the spacer can be reached. It should be possible to move the measuring head along the measuring openings. The varying thicknesses of different spacers and also the varying thickness ranges of one single spacer require that the measuring head be movable with respect to height, i.e. perpendicular to the spacer. Mobility in this spatial direction is also advantageous when the measuring head is to be lowered onto the spacer from a resting position. The measuring head may be rigidly adjusted with respect to the third spatial direction, or it may be given a limited mobility, if adjustment is achieved via a guide rail at the spacer above the measuring opening.

The evaluation device in accordance with the invention also comprises a test element support onto which the test element to be analyzed is placed. This test element support can be a flat surface which is planar and mechanically supports the test element at least in the area carrying the test fields. It is preferred to have a stable test strip support, it may, however, also be movable. By exerting pressure onto the spacer, it should be able to place the test strip support into defined end position.

An essential aspect of the invention is the spacer as it allows the evaluation of individual test fields in a defined distance. The spacer essentially has the form of a longitudinal plate with a length of a few centimeters, a width of a few centimeters, and a thickness of a few millimeters. The spacer is preferably configured as an integral plastic piece. Particularly suitable plastics are polyoxymethylene and polyphenylene oxide.

On the surface of the spacer, provision is made for measuring openings. Radiation is sent through these measuring openings onto the test fields of a test element, and the reflected radiation also passes through these measuring openings. The measuring openings are arranged such that the test fields of a test element located underneath are accessible. This means that the arrangement of the measuring openings corresponds to the arrangement of the test fields on the test elements. It is preferred that the size and shape of the measuring openings be such that the test fields are completely accessible, but that they do not essentially exceed the test fields in order to reduce interfering signals from the edges as far as possible. The measuring openings are preferably rectangular and are tapered from the side facing the measuring head toward the side facing the test strip.

The measuring openings are preferably recesses in the spacer which are surrounded by the spacer. Possible measuring openings are also those recesses that are only partly surrounded by the spacer and are open toward an edge of said spacer.

A particularly preferred embodiment of the spacer is one having a vertical profile. Experience has shown that for an improved measuring accuracy it is advantageous to have a defined distance between the surface of the test field and the measuring head, said distance being identical for each test field. This is important as the measured intensity of the reflected radiation greatly depends on this distance. In conventional test strips, different test fields have different thicknesses which, however, are known with a relatively great degree of accuracy. The resulting problem is that the distances between the upper edge of the test field and the measuring head vary as the measuring head is moved at a constant distance with respect to the test elements. As already mentioned, this leads to inaccuracies in the measurement which cannot be sufficiently accounted for mathematically. Experience has shown that it is most favorable to have a constant distance between the surface of the test fields and the measuring head. This is achieved by the vertical profile of the spacer. Each test field is associated with a measuring opening and a support area for the measuring head. With the test field and its thickness being known, the area of the spacer associated with this test field, especially the contact area of measuring head and spacer, can be selected with respect to thickness such that a given distance between measuring head and test field surface is maintained.

When the measurement is carried out, the measuring head rests with one edge on the spacer. Because of the varying heights of the vertical profile at the site of contact of the measuring head, it is possible to have a constant, predetermined value for the distance between the test field surface and the measuring head for each test field. The spacer preferably has strip-like areas with each area being associated with a measuring opening. It has proven to be advantageous if each one of these areas has a level of constant height with adjacent levels being connected to each other by slanted surfaces.

During the evaluation procedure, a contact pressure device exerts pressure onto the arrangement consisting of spacer, test element, and test element support. Only the tolerances resulting from the spacer or the support edge of the measuring head are, hence, relevant to the distance between test field surface and measuring head. Experience has shown that this sandwich arrangement of the test element between spacer and test strip support allows a considerably more accurate evaluation than presently known measuring arrangements.

A contact pressure device in accordance with the invention can be accomplished, for example, in that the measuring head exerts pressure onto the spacer as a consequence of its own weight. It is preferred in accordance with the invention to have a spring construction where the measuring head is attached to the instrument base via a lever. The lever is arranged perpendicularly to the longitudinal axis of the spacer. Owing to the length of the lever in an order of magnitude of more than one decimeter there is, hence, no considerable rotation of the optical unit when the measuring head is moved over the profile of the spacer. To avoid tilting of the measuring head, a contact edge on the spacer is selected for the measuring head to rest on the spacer. This contact edge preferably has a width that is smaller than the previously described levels of the vertical profile on the spacer. The described arrangement ensures that the measuring head follows the vertical profile during a relative movement of measuring head and spacer without considerable tilting of the optical unit.

With the described lever construction, the lever can be pressed on the arrangement of spacer, test element, and test element support via a spring. The spring is attached to the lever, on the one side, and the base of a lever support, on the other side.

The relative guidance of measuring head and spacer can further be improved by providing a guide rail at the spacer. Purpose of the guide rail is that the measuring head is located above the center of a measuring position in the direction perpendicularly to the longitudinal axis of the spacer. Because of this arrangement, the effort for positioning the spacer can further be reduced.

The performance of the spacer can further be improved by providing a recess for holding the test element at the lower side of the spacer, i.e. at the side facing toward the test element. In said recess, there are cross bars provided between two adjacent measuring openings. Purpose of these cross bars is to press the test element onto the test element support and to eliminate interfering radiation from adjacent test fields. It is preferred to have relatively small cross bars, or ones that are tapered in direction toward the test strip to minimize the contact area with the test element. This is of importance to avoid carry-overs from one test element to the next.

In order to examine the various test fields of a test element, measuring head and test element must execute a relative movement. In a preferred manner, the arrangement of spacer, test element and test element support remains unchanged, while a drive motor moves the measuring head in a direction toward the longitudinal axis of the test element.

The invention also includes a method for evaluating test elements where a test element is located between the test element support and a spacer with a vertical profile and measuring openings. A measuring head with emitter and sensor is moved along the measuring opening of the spacer to measure the remission values of the test fields of the test element.

In order to implement the method of the invention, the above described evaluation device is used. In order to evaluate a test element, each test field can be evaluated with only one measuring head as already described above, or the evaluation can be carried out with several measuring heads where each head uses one specific type of radiation. It is thus possible to evaluate individual test fields with varying wavelengths.

Moreover, it is also possible to provide an array of measuring heads instead of one single head. In this array, the individual heads can be moved with respect to each other and each measuring head is at a defined distance to the respective test field surface while being controlled by the spacer.

A central aspect of the invention is the spacer for evaluating test elements which has one or several measuring openings that are disposed next to each other. Said spacer also has a vertical profile with a constant thickness within the area of the contact surface associated with a given measuring opening while the contact surfaces associated with varying measuring openings have varying thicknesses.

As opposed to prior art, the present invention has the advantages that the technical complexity for adjusting the device is greatly reduced due to the use of a spacer, and a given setting of the instrument can be maintained over an extended operation period. Moreover, it is also an advantage of the invention that test fields with varying thicknesses can be evaluated with only one measuring head. An adjustment to account for numerous different measuring heads is, hence, not required.

The so far generally described invention is now illustrated in greater detail with respect to the following figures:

FIG. 1: evaluation device

Figure 2:
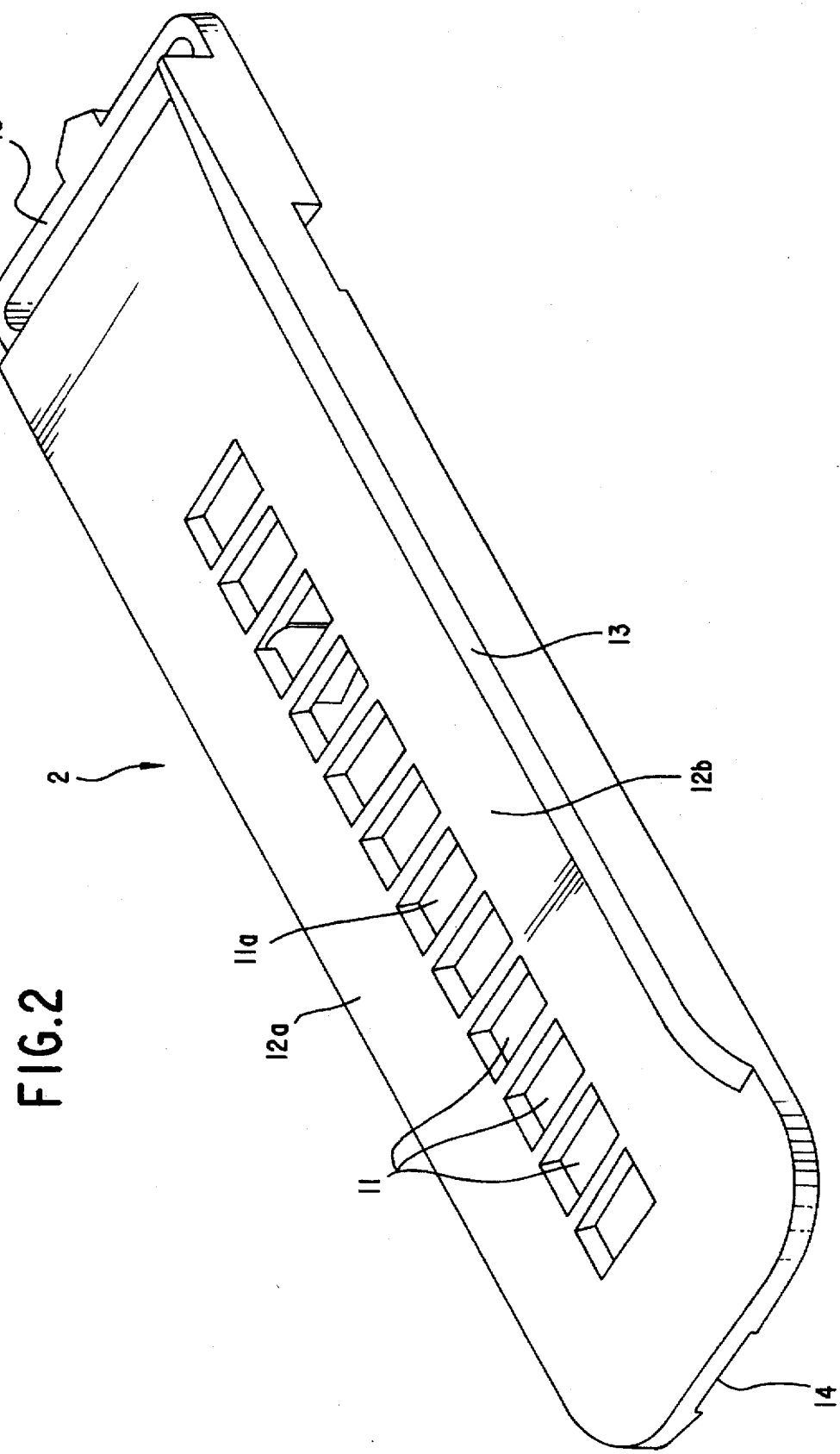

FIG. 2: spacer (top side)

FIG. 3: spacer (bottom side)

FIG. 1 shows an evaluation device (1) in accordance with the invention having a measuring head (3), and an arrangement of spacers (2), test strips (20), and test element support (4). From the figure it can be understood that test field (21a) has a smaller thickness than test field (21b). Above test field (21b), the spacer has a larger thickness than above test field (21a). It can also be understood that the vertical profile of spacer (2) has levels (6, 7) that run parallel to the test strip support (4). Both levels (6, 7) are connected via a slanted surface, so that the measuring head can be pushed from level (6) to level (7) without the risk of jamming. The measuring head is moved over the test strip with the aid of a drive motor. During the entire measurement, a parallel leaf spring (9) presses the measuring head (3) onto the spacer (2). In order to exert a certain contact pressure onto test strip (20), spacer (2) is provided with cross bars (8) that run between the measuring openings of the spacer. This ensures that the test strip is pressed onto the support in the area of the test fields.

FIG. 2 shows a spacer (2) in accordance with the invention with a multitude of measuring openings (11). Each measuring opening is associated with level of the spacer; level (12) which consists of two parts (12a, 12b) is associated with measuring opening (11a), for example. During the measurement, the edge of the support of the measuring head rests on one of the surfaces (12a or 12b).

FIG. 2 shows a guide rail (13) that positions the measuring head above a measuring opening.

A recess (14) in which the test element comes to rest is also shown on the bottom side of the spacer (2).

To insert the spacer (2) in an evaluating instrument, spacer (2) is provided with a handle (15).

FIG. 3 is a bottom view of spacer (2). The figure shows the cross bars (8) and guide elements (10) which are in contact with a test strip when such a strip is placed underneath the spacer. In order to match these guide elements, test element support (4) is provided with recesses, so that the guide elements do not affect the distance between the spacer and test element support.

For additional information regarding a related invention, reference should be made to a patent application entitled "Evaluation Instrument for Test Strips with a Transport Unit for Test Strips", invented by Mr. Manfred Augstein, filed on even date herewith, and given U.S. patent application Ser. No. 08/503,693.

LIST OF REFERENCE NUMERALS (1) Evaluation device
(2) Spacer
(3) Measuring head
(4) Test element support
(6, 7) Levels
(8) Cross bars
(9) Parallel leaf spring
(10) Guide elements
(11, 11a) Measuring openings
(12a, 12b) Level
(13) Guide rail
(14) Recess
(15) Handle
(20) Test element
(21a, 21b) Test field surface

I claim:

1. A device for reflectometric evaluation of test elements wherein each test element includes a plurality of adjacent test fields thereupon, said device comprising:

measuring means for performing a reflectometric evaluation;

support means for supporting a test element thereupon, said support means being disposed adjacent said measuring means;

spacer means for spacing said measuring means a defined distance from at least one surface of said plurality of adjacent test fields, said spacer means being located between the test element on said support means and said measuring means, and having at least one measuring opening therein, wherein said at least one measuring opening provides access to the test element by the measuring means, and wherein an upper surface of the spacer means comprises a plurality of levels having a plurality of different heights for supporting the measuring means at said defined distance above the test element, corresponding to surfaces of the plurality of adjacent test fields.

2. A device as recited in claim 1, wherein said measuring means comprises a measuring head having an emitter and a sensor thereupon, said emitter for emitting a measurement signal and said sensor for sensing a portion of the measurement signal being reflected from the test element.

3. A device as recited in claim 1, further comprising a contact pressure means for pressing the measuring means onto the spacer means, wherein the pressure is received by the spacer means, the test element, and the support means.

4. A device as recited in claim 1, wherein said plurality of levels are formed by a varying cross-sectional thickness of the spacer means.

5. A device as recited in claim 1, wherein said at least one measuring opening is configured to correspond to one of said plurality of adjacent test fields.

6. A device as recited in claim 1, wherein said at least one measuring opening has a rectangular periphery.

7. A device as recited in claim 1, wherein said spacer means includes a guide means on a surface thereof opposed to said measuring means, said guide means for guiding the measuring means thereupon.

8. A device as recited in claim 1, wherein said spacer means includes a recess on a bottom side thereof, said recess being configured to accommodate the test element therein.

9. A device as recited in claim 1, wherein said spacer means includes a plurality of cross bars on a bottom side thereof, said cross bars separating each of said plurality of adjacent test fields.

10. A device as recited in claim 9, wherein said at least one measuring opening is configured between two of said plurality of cross bars.

11. A device as recited in claim 1, further comprising drive means for moving the measuring head along the upper surface of said spacer means.

12. A device as recited in claim 11, wherein said spacer means includes a plurality of measuring openings therein, and said drive means drives said measuring means from one of said plurality of measuring openings to another of said plurality of measuring openings.

13. A device as recited in claim 1, wherein the distance between a surface of each of said plurality of test fields and a contact surface of said spacer means is essentially constant from one of said plurality of test fields to another of said plurality of test fields.

* * * * *